United States Patent
Brown

(10) Patent No.: US 7,297,109 B2
(45) Date of Patent: Nov. 20, 2007

(54) METHOD AND SYSTEM FOR IMPROVING ADHERENCE WITH A DIET PROGRAM OR OTHER MEDICAL REGIMEN

(75) Inventor: Stephen J. Brown, Woodside, CA (US)

(73) Assignee: Health Hero Network, Inc., Mountain View, CA (US)

( * ) Notice: Subject to any disclaimer, the term of this patent is extended or adjusted under 35 U.S.C. 154(b) by 220 days.

(21) Appl. No.: 10/319,427

(22) Filed: Dec. 12, 2002

(65) Prior Publication Data

US 2004/0116780 A1 Jun. 17, 2004

Related U.S. Application Data

(63) Continuation of application No. 09/713,922, filed on Nov. 15, 2000, now abandoned, which is a continuation-in-part of application No. 09/422,046, filed on Oct. 20, 1999, which is a continuation of application No. 09/271,217, filed on Mar. 17, 1999, now Pat. No. 6,168,563, which is a continuation-in-part of application No. 08/481,925, filed on Jun. 7, 1995, now Pat. No. 5,899,855, which is a continuation of application No. 08/233,397, filed on Apr. 26, 1994, now abandoned, which is a continuation-in-part of application No. 07/977,323, filed on Nov. 17, 1992, now Pat. No. 5,307,263, application No. 10/319,427, which is a continuation-in-part of application No. 09/237,194, filed on Jan. 26, 1999, which is a continuation of application No. 08/481,925, filed on Jun. 7, 1995, now Pat. No. 5,899,855.

(60) Provisional application No. 60/165,818, filed on Nov. 16, 1999.

(51) Int. Cl.
*A61B 5/00* (2006.01)

(52) U.S. Cl. ........................................ 600/300; 128/921

(58) Field of Classification Search .................. 600/300, 600/301; 128/920–925; 705/2–4, 10, 15; 235/375, 385; 482/8–9
See application file for complete search history.

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |
| 3,768,014 A | 10/1973 | Smith |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,130,881 A | 12/1978 | Haessler et al. |

(Continued)

FOREIGN PATENT DOCUMENTS

| | | |
|---|---|---|
| EP | 0251520 | 7/1988 |
| EP | 0286456 | 10/1988 |
| EP | 0320749 | 2/1989 |
| EP | 370599 | 5/1990 |
| EP | 0461910 | 12/1991 |
| EP | 508912 | 10/1992 |
| EP | 526166 | 2/1993 |
| EP | 0653718 | 11/1994 |
| EP | 676709 | 10/1995 |

(Continued)

*Primary Examiner*—Mary Beth Jones
*Assistant Examiner*—Michael Astorino
(74) *Attorney, Agent, or Firm*—Patton Boggs LLP

(57) ABSTRACT

A method, system and computer program product for remotely measuring one's adherence to a diet program while making it convenient and easy to place food orders, and learn about and try new foods that are acceptable to the diet program. The system includes a user system with a processor, memory and at least one user interface device, a server system with a processor and memory, and a food delivery system coupled to the server system over the network.

13 Claims, 2 Drawing Sheets

U.S. PATENT DOCUMENTS

| | | |
|---|---|---|
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,417,306 A | 11/1983 | Citron et al. |
| 4,422,081 A | 12/1983 | Woods |
| 4,449,536 A | 5/1984 | Weaver |
| 4,465,077 A | 8/1984 | Schneider |
| 4,473,884 A | 9/1984 | Behl |
| 4,519,398 A | 5/1985 | Lisiecki et al. |
| 4,531,527 A | 7/1985 | Reinhold, Jr. et al. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,731,726 A | 3/1988 | Allen, III |
| 4,768,229 A | 8/1988 | Benjamin et al. |
| 4,779,199 A | 10/1988 | Yoneda et al. |
| 4,782,511 A | 11/1988 | Nemec et al. |
| 4,796,639 A | 1/1989 | Snow et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,858,354 A | 8/1989 | Gettler |
| 4,858,617 A | 8/1989 | Sanders |
| 4,890,621 A | 1/1990 | Hakky |
| 4,897,869 A | 1/1990 | Takahashi |
| 4,907,973 A | 3/1990 | Hon |
| 4,933,873 A | 6/1990 | Kaufman et al. |
| 4,950,246 A | 8/1990 | Muller |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,979,509 A | 12/1990 | Hakky |
| 5,007,429 A | 4/1991 | Treatch et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,095,798 A | 3/1992 | Okada et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,176,502 A | 1/1993 | Sanderson et al. |
| 5,182,707 A | 1/1993 | Cooper et al. |
| 5,204,670 A | 4/1993 | Stinton |
| 5,222,020 A | 6/1993 | Takeda |
| 5,227,874 A | 7/1993 | Von Kohorn |
| 5,228,450 A | 7/1993 | Sellers |
| 5,231,990 A | 8/1993 | Gauglitz |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,299,121 A | 3/1994 | Brill et al. |
| 5,301,105 A | 4/1994 | Cummings, Jr. |
| 5,304,468 A | 4/1994 | Phillips |
| 5,307,263 A | 4/1994 | Brown |
| 5,309,919 A | 5/1994 | Snell et al. |
| 5,329,459 A | 7/1994 | Kaufman et al. |
| 5,329,608 A | 7/1994 | Bocchieri et al. |
| 5,331,549 A | 7/1994 | Crawford, Jr. |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,691 A | 7/1995 | Snell et al. |
| 5,434,611 A | 7/1995 | Tamura |
| 5,438,607 A | 8/1995 | Przygoda, Jr. et al. |
| 5,441,047 A | 8/1995 | David et al. |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,467,269 A | 11/1995 | Flaten |
| 5,471,039 A | 11/1995 | Irwin, Jr. et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,433 A | 5/1996 | Lappington et al. |
| 5,544,649 A | 8/1996 | David et al. |
| 5,546,943 A | 8/1996 | Gould |

| | | |
|---|---|---|
| 5,549,117 A | 8/1996 | Tacklind et al. |
| 5,550,575 A | 8/1996 | West et al. |
| 5,553,609 A | 9/1996 | Chen |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,574,828 A | 11/1996 | Hayward et al. |
| 5,576,952 A | 11/1996 | Stutman et al. |
| 5,590,648 A | 1/1997 | Mitchell et al. |
| 5,596,994 A | 1/1997 | Bro |
| 5,597,307 A | 1/1997 | Redford et al. |
| 5,601,435 A | 2/1997 | Quy |
| 5,613,495 A | 3/1997 | Mills et al. |
| 5,619,991 A | 4/1997 | Sloane |
| 5,624,265 A | 4/1997 | Redford et al. |
| 5,628,309 A | 5/1997 | Brown |
| 5,629,981 A | 5/1997 | Nerlikar |
| 5,631,844 A | 5/1997 | Magrey et al. |
| 5,633,910 A | 5/1997 | Cohen |
| 5,640,953 A | 6/1997 | Bishop et al. |
| 5,642,731 A | 7/1997 | Kehr |
| 5,642,936 A | 7/1997 | Evans |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,687,322 A | 11/1997 | Deaton et al. |
| 5,687,717 A | 11/1997 | Halpern et al. |
| 5,687,734 A | 11/1997 | Dempsey et al. |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,711,297 A | 1/1998 | Iliff |
| 5,715,451 A | 2/1998 | Marlin |
| 5,715,823 A | 2/1998 | Wood et al. |
| 5,717,913 A | 2/1998 | Driscoll |
| 5,720,733 A | 2/1998 | Brown |
| 5,722,418 A | 3/1998 | Bro |
| 5,727,153 A | 3/1998 | Powell |
| 5,730,124 A | 3/1998 | Yamauchi |
| 5,732,696 A | 3/1998 | Rapoport et al. |
| 5,732,709 A | 3/1998 | Tacklind et al. |
| 5,734,413 A | 3/1998 | Lappington et al. |
| 5,752,234 A | 5/1998 | Withers |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,791,342 A | 8/1998 | Woodard |
| 5,792,117 A | 8/1998 | Brown |
| 5,793,969 A | 8/1998 | Kamentsky et al. |
| 5,796,393 A | 8/1998 | MacNaughton et al. |
| 5,802,494 A | 9/1998 | Kuno |
| 5,819,735 A | 10/1998 | Mansfield et al. |
| 5,822,544 A | 10/1998 | Chaco et al. |
| 5,825,283 A | 10/1998 | Camhi |
| 5,827,180 A | 10/1998 | Goodman |
| 5,828,943 A | 10/1998 | Brown |
| 5,835,896 A | 11/1998 | Fisher et al. |
| 5,868,669 A | 2/1999 | Iliff |
| 5,875,432 A | 2/1999 | Sehr |
| 5,879,163 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofbert et al. |
| 5,933,136 A | 8/1999 | Brown |
| 5,941,829 A | 8/1999 | Saltzstein et al. |
| 5,961,446 A | 10/1999 | Beller et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 6,001,065 A | 12/1999 | DeVito |
| 6,022,315 A | 2/2000 | Iliff |
| 6,022,615 A | 2/2000 | Rettenbacher |
| 6,024,281 A * | 2/2000 | Shepley ...................... 235/375 |
| 6,029,138 A | 2/2000 | Khorasani et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,110,148 A | 8/2000 | Brown et al. |
| 6,138,145 A | 10/2000 | Kawanaka |
| 6,151,586 A | 11/2000 | Brown |
| 6,168,563 B1 | 1/2001 | Brown |
| 6,177,940 B1 | 1/2001 | Bond et al. |
| 6,189,029 B1 | 2/2001 | Fuerst |
| 6,221,012 B1 | 4/2001 | Maschke et al. |
| 6,248,065 B1 | 6/2001 | Brown |
| 6,368,273 B1 | 4/2002 | Brown |
| 6,370,513 B1 * | 4/2002 | Kolawa et al. ................ 705/10 |
| 6,436,036 B1 * | 8/2002 | Miller-Kovach et al. ... 600/300 |
| 6,513,532 B2 * | 2/2003 | Mault et al. ................ 600/595 |

FOREIGN PATENT DOCUMENTS

| | | |
|---|---|---|
| EP | 680727 | 11/1995 |
| EP | 761160 | 3/1997 |
| GB | 2218831 | 11/1989 |
| GB | 2225637 | 6/1990 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9529447 | 11/1995 |
| WO | WO-96/07908 | 3/1996 |
| WO | WO-96/25877 | 8/1996 |
| WO | WO-97/08605 | 3/1997 |
| WO | WO-97/12544 | 4/1997 |
| WO | WO-98/16895 | 4/1998 |

* cited by examiner

METHOD AND SYSTEM FOR IMPROVING ADHERENCE WITH A DIET PROGRAM OR OTHER MEDICAL REGIMEN

This application is a continuation of U.S. application Ser. No. 09/713,922 filed Nov. 15, 2000, now abandoned, which claims the benefit of U.S. Provisional Application No. 60/165,818 filed Nov. 16, 1999. This application is also a Continuation-in-Part of a U.S. application Ser. No. 09/422,046 filed Oct. 20, 1999, which is a continuation of U.S. application Ser. No. 09/271,217 filed Mar. 17, 1999, now U.S. Pat. No. 6,168,563, which is a Continuation-In-Part of U.S. patent application No. 08/481,925 filed Jun. 7, 1995, now U.S. Pat. No. 5,899,855, which is a Continuation of U.S. application Ser. No. 08/233,397 filed Apr. 26, 1994, now abandoned, and is a Continuation-in-Part of U.S. application Ser. No. 07/977,323 filed Nov. 17, 1992, now U.S. Pat. No. 5,307,263. U.S. application Ser. No. 09/271,217 is also a Continuation-in-Part of U.S. application No. 08/946,341, filed Oct. 7, 1997, now U.S. Pat. No. 5,997,476, which is a Continuation-in-Part of U.S. application No. 08/847,009, filed Apr. 30, 1997, now U.S. Pat. No. 5,897,493, which claims the benefit of U.S. Provisional Application No. 60/041,746, filed Mar. 28, 1997 and U.S. Provisional Application No. 60/041,751, filed Mar. 28, 1997.

This application is also a Continuation-in-Part of U.S. Ser. No. 09/237,194 filed on Jan. 26, 1999, which is a Continuation of U.S. patent application No. 08/481,925 filed Jun. 7, 1995, now U.S. Pat. No. 5,899,855, which is a Continuation of U.S. application Ser. No. 08/233,397 filed on Apr. 26, 1994, now abandoned, and is a Continuation-in-Part of U.S. application Ser. No. 07/977,323 filed Nov. 17, 1992, now U.S. Pat. No. 5,307,263.

All of the above named applications are hereby incorporated by reference.

BACKGROUND OF THE INVENTION

1. Field of the Invention

This application is related to U.S. Ser. No. 09/293,363 filed on Apr. 16, 1999 abandoned, U.S. Ser. No. 09/203,882 filed on Dec. 1, 1998 abandoned, U.S. Ser. No. 09/159,219 filed on Sep. 23, 1998 abandoned, U.S. Ser. No. 09/159,058 filed on Sep. 23, 1998 abandoned, U.S. Ser. No. 09/203,880 filed Dec. 1, 1998 abandoned, U.S. Ser. No. 09/201,323 filed on Nov. 30, 1998 abandoned, U.S. Ser. No. 09/320,004 filed on May 26, 1999 abandoned, U.S. Ser. No. 09/318,708 filed on May 26, 1999 abandoned, U.S. Ser. No. 09/274,433 filed on Mar. 22, 1999 now abandoned, U.S. Ser. No. 09/201,372 filed on Nov. 30, 1998 abandoned, U.S. Pat. No. 5,879,163, U.S. Pat. No. 6,151,586, U.S. Pat. No. 5,933,136, U.S. Ser. No. 09/531,237 filed Mar. 21, 2000 abandoned, U.S. Pat. No. 6,368,273, U.S. Pat. No. 5,997,476, U.S. Pat. No. 5,897,493, U.S. Ser. No. 09/518,426 filed Mar. 3, 2000 now abandoned, U.S. Pat. No. 6,068,615, U.S. Pat. No. 5,782,814, U.S. Pat. No. 5,569,212, U.S. Ser. No. 09/495,809 filed Feb. 1, 2000 abandoned, U.S. Pat. No. 6,186,145, U.S. Pat. No. 5,913,390, U.S. Pat. No. 5,918,603, U.S. Pat. No. 5,678,571, U.S. Ser. No. 09/495,809, U.S. Pat. No. 5,997,476, U.S. Pat. No. 5,897,493, U.S. Pat. No. 6,334,778, U.S. Pat. No. 5,940,801, U.S. Pat. No. 5,828,943, U.S. Ser. No. 08/682,385 filed Jul. 17, 1996 now abandoned, U.S. Ser. No. 08/233,674 filed Apr. 26, 1994 now abandoned, U.S. Pat. No. 6,240,393, U.S. Pat. No. 6,023,686, U.S. Pat. No. 5,887,133, U.S. Pat. No. 5,794,219, U.S. Pat. No. 6,246,992, U.S. Pat. No. 5,832,448, U.S. Pat. No. 6,167,386, U.S. Pat. No. 6,023,686, U.S. Pat. No. 5,794,219, U.S. Pat. No. 5,887,133, U.S. Pat. No. 5,794,219, U.S. Pat. No. 5,887,133, U.S. Ser. No. 09/441,408 filed Nov. 16, 1999 now abandoned, U.S. Ser. No. 10/024,445 filed Dec. 17, 2001, now abandoned, U.S. Pat. No. 6,196,970, U.S. Pat. No. 6,330,426, U.S. Ser. No. 08/953,883 filed Oct. 20, 1997 now abandoned, U.S. Pat. No. 6,144,837, U.S. Pat. No. 5,601,435, U.S. Pat. No. 6,330,426, U.S. Pat. No. 5,913,310, U.S. Pat. No. 5,918,603, U.S. Pat. No. 5,678,571, and U.S. Pat. No. 6,210,272. All of the above named applications are hereby incorporated by reference.

This invention relates to an interactive computerized system and process for behavior analysis and feedback, and more particularly to a system for monitoring intake and providing feedback according to a plan.

Diet and lifestyle are key factors in chronic medical conditions such as obesity, cardiovascular disease, diabetes, cancer, and many other conditions. As a result, there are hundreds of diets—fad diets, celebrity promoted diets, and medically based diets. Yet as a whole, Americans still eat a high fat, high calorie, junk food diet. Also, diet programs are notorious for the poor adherence by the dieters.

A problem with existing diets, weight loss programs, and healthy regimens is that the diets are very difficult to faithfully follow, or adhere to. The task of keeping track of what is healthy or required by the diet is so tedious that, as a result, many diet program participants return to fatty foods simply for convenience and lack of sufficient interest to overcome the tedium. Another problem is that the present systems do not provide enough measurement and feedback to let one know how they are progressing. Even with diet programs that require the dieter to visit a center to weigh in, the dieters are nevertheless on their own most of the time. Finally, food labeled as healthy food is usually more expensive than fattier foods.

The following patents are examples of the prior art discussed above.

U.S. Pat. No. 5,890,128 to Diaz et al. discloses hand held individually customized interactive integrated circuit device for nutrition and exercise management. The device of Diaz et al. includes built in storage of extensive food lists with associated caloric and fat contents. Diaz et al. incorporates storage of exercises with associated activity caloric values or rates. Diaz et al. utilizes the individual's personal characteristics such as sex, age, weight, height, frame size, life style and goals with programmed calculations to derive optimum suggested weight, metabolic rate, daily caloric/fat intake targets, exercise targets and exercise/daily calorie burning rates. Diaz et al. tracks daily and historical individual caloric input/output, fat input, and weight which can be viewed in the form of charts and graphs. Optional medical programs take into consideration special dieting, medication and exercise requirements of patients with diabetes, high cholesterol, heart ailments, hypoglycemia and other diseases. Diaz et al. is good at tracking historical data but fails to provide a system that will automatically generate a food order for home delivery based on the derived information.

U.S. Pat. No. 5,673,691 to Abrams, et al. discloses a hand-held computer that prepares and monitors a goal-oriented weight, nutrition and exercise control program. Visual and audio prompts tell users when to eat and exercise, and provide suggestions for what to eat. Abrams et al. teaches assisting the user in setting safe goals for desired weight loss and the time required to achieve the loss. The user follows menu and exercise programs suggested by the system. The system records and analyzes the user's food consumption, exercise and weight loss programs. Finally, the computer displays feedback information regarding the user's progress towards achieving the desired weight. If the users have planned which meals they will select from a set of future recommendations, then the planned meals can be presented in such a way as to make selection and recording of the meals simple and quick. Also, meal planning allows the Behavior Planning routine to build a shopping list for the users to ensure they will have the necessary food on hand to prepare planned meals.

Diaz et al. is good tool for locally administering a weight loss program, however it fails to provide a system used for controlling diets for other medical purposes that will automatically generate a food order and make suggestions according to food pricing and availability information from a food delivery system.

What is needed is a system and method to measure a healthy diet while making it convenient and easy to place orders, learn about and try new foods that are acceptable to their diet program and their measured intake.

SUMMARY OF THE INVENTION

The present invention provides a method, system and computer program product for remotely measuring one's adherence to a diet program while making it convenient and easy to place food orders, and learn about and try new foods that are acceptable to the diet program. The system includes a user system with a processor, memory and at least one user interface device, a server system with a processor and memory, and a food delivery system coupled to the server system over the network.

The server system generates and sends a query to the user system, the server system determines diet program information for a user associated with the user system based upon responses to the query sent from the user system to the server system, and user profile information, and generates a food delivery request according to the determined diet program information. The food delivery system prepares a food order according to the food list, delivers the food order to the user, and sends a record of the food order to the server system. The server stores the record of the food order.

In accordance with other aspects of the present invention, the user interface is a medical monitoring device.

In accordance with still other aspects of the present invention, the server processor includes a diet suggestion component for suggesting one or more alternate food items for one or more of the selected food items.

In accordance with further aspects of the present invention, the user interface allows for entry of point values for food items consumed. The server system receives point values from the user system, compares the received point values to predetermined meal plan limits and creates a meal plan according to the comparison.

In accordance with yet further aspects of the present invention, the user interface is a bar code scanner for scanning a bar code present on packages of user consumed food items. The server system includes a component that receives scanned bar code information from the user system, automatically orders refills according to program information, records the scanned food item as being consumed and updates the program information according to the recorded scanned food item.

As will be readily appreciated from the foregoing summary, the invention provides a food intake monitoring system with automatically delivery of food based on user preferences and user diet goals.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
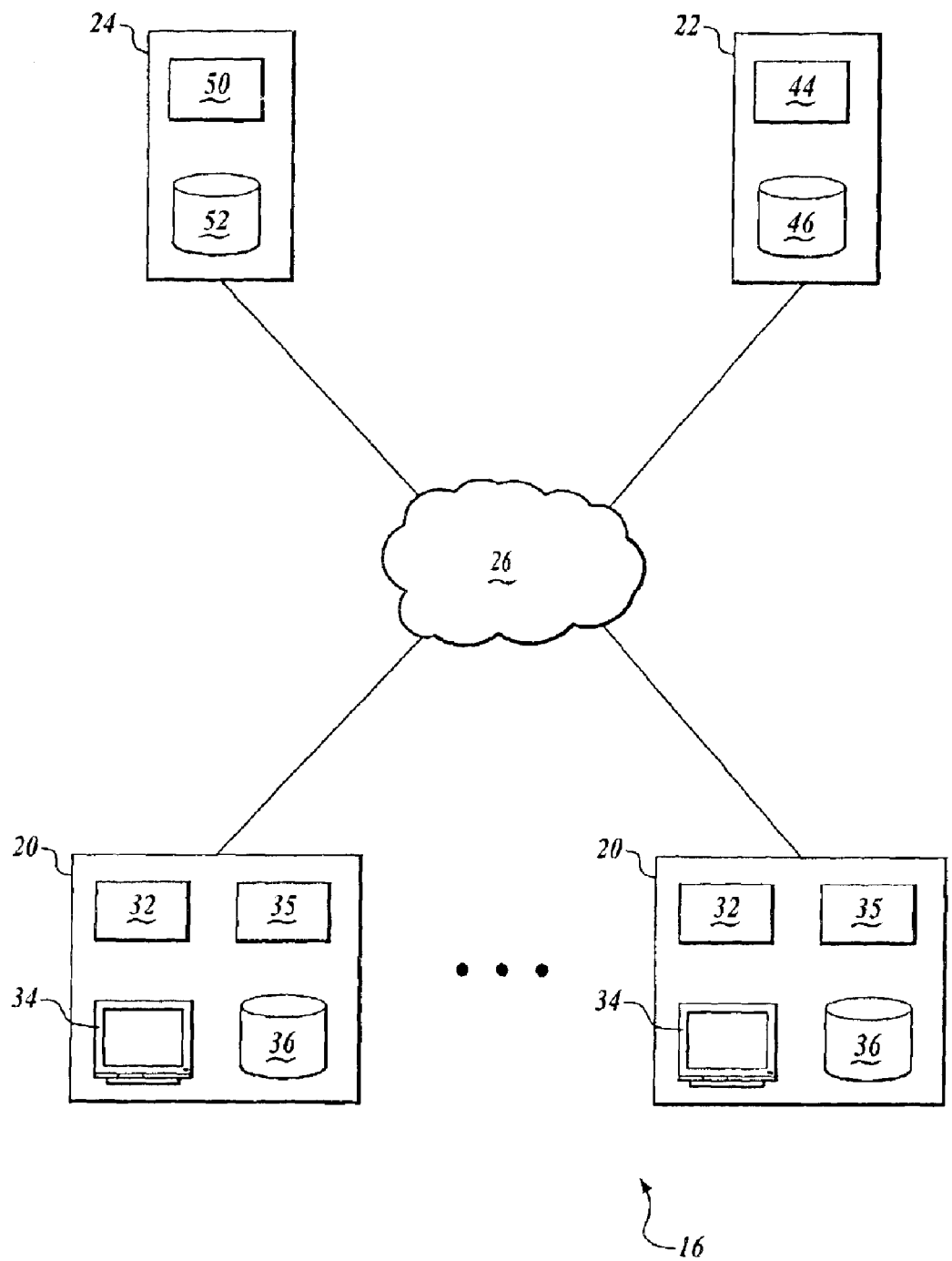
FIG. 1 is a block diagram of the present invention.

As shown in FIG. 1, the present invention includes a plurality of user devices 20, a program server 22 and a delivery system 24, all of which are coupled to a public or private communication network 26. The user devices 20 can be of varying types as will be described in more detail below.

The user device 20 is a computer device that includes a processor 32 and a display 34, an input device 35 and memory 36 coupled to the processor 32. The processor 32 couples to the public or private communication network 26 via network accessibility software pre-stored in the memory 36.

The user devices 20 use the display 34 to inform the users that input information is desired. The user is a patient, a caregiver for the patient, or some other person requiring program information, such as diet program information. Preferably, the display 34 includes an alphanumeric display capable of displaying questions corresponding to the user or patient. The user device 20 receives from the user using the input device 35 answers to the displayed questions. For example, if the displayed question asks what is the user's/patient's weight that day, the user enters the patient's weight into the user device 20 using the input device 35.

The input device 35 includes a keypad or keyboard, such as a television remote control, or is a keypad with a restricted set of keys by which the user increments, decrements, or accepts a value to be entered for the patient, such as the patient's weight for that day. In an alternate embodiment, the input device 35 is a monitoring device that generates a monitored signal and automatically sends the monitored signal to the processor 32. The type of monitoring device used by each user is dependent upon the user's diet. For example, for a weight loss patient, the monitoring device is a weight scale. For a diabetes patient, the monitoring device is a blood glucose meter for measuring the patient's blood glucose concentrations. For an asthma patient, the monitoring device is a peak flow meter for measuring the patient's peak flow rates. Such monitoring devices for recording and transmitting measurements are well known in the art.

Alternative embodiments of the user device 20 may include a wide variety of other devices, possibly including electronic toy (such as a "key employee" or "virtual pet"), a telephone in connection with an interactive voice response system, a television set-top box interacting with a cable or satellite television interactive system, a medical device operated at a medical personal office, or any other system by which the user can enter information to be used by the program server 22.

In one embodiment, the public or private communication network 26 is the Internet. The messages sent between the program server 22 and the user devices 20 over the Internet are formatted using a communication protocol, such as TCP/IP, HTML, or a combination thereof. The public or private communication network 26 can also be a direct connection via a modem or some other means, a local area network or a comparable communication network.

The program server 22 includes a processor 44 and memory 46. The program server 22 determines diet program information for each user based on user profile information prestored in the memory 46 and the information received from the user devices 20.

Also referring to FIG. 1, the delivery system 24 also includes a processor 50 and memory 52 for processing food delivery requests from the user devices 20 or the program server 22. An example of a delivery system coupled to users over a public network are Internet or web grocers that compile and deliver food orders based on food lists received from an order executed over the Internet.

The processor 44 of the program server 22 includes a program application previously installed. The program application is a controlling software application executed by server 22 that includes the following components: a script generator; a script assignor; and a report generator. The script generator generates script programs from script information previously entered by a program server coordinator or health care professional. The script programs are executed on the user devices 20 to display queries to the users, receive responses to the displayed queries, collect monitoring device measurements and transmit responses and measurements to the program server 22. The memory 46 in the program server 22 stores the responses and measurements. The memory 46 includes a look-up table that contains a list of the patients to be monitored and for each patient, a corresponding patient identification code and a respective pointer to at least one script program assigned to the patient.

The program application also includes a database, a diet composer component and a diet suggestion component. The database is stored in memory 46 and includes program information. The program information includes food items, patient food preferences, recipes with dietary information such as calories and fat content, model meal plans and patient profile information. The patient profile information includes weight history, weight goals, food history, food preferences, demographic information and patient shopping lists. The diet composer component selects food items based on the model meal plan, patient food preferences, patient profile information and patient information entered via the input device 35 and food cost and availability information provided by the delivery system 24. The diet suggestion component suggests new food items or substitutions in the model meal plan based on the selected food items. The components of the program application can be distributed over the system—the delivery system 24 or the user devices 20.

In an alternate embodiment, the application program includes a point system component that asks a user to enters points associated with certain foods. The point system component compares the amount of entered points to predetermined meal plan limits and creates meal plans according to this comparison.

In still another embodiment, the input device 35 of the user device 20 includes a bar code scanner that allows users to scan the bar code present on food packages to record food usage or automatically order refills. The processor 32 and memory 36 in the user device 20 further includes a program that retrieves prestored information pertaining to the food package scanned. The program records the retrieved information as being consumed by the user, being requested by the user for reorder, or being used for some other purpose.

The program server 22 also generates a program adherence value. The program adherence value is a value that indicates how well the patient is adhering to the program. The program adherence value is calculated according the patient's determined diet or meal plan, predefined goals, the patient's food intake and other input information.

Figure 2:
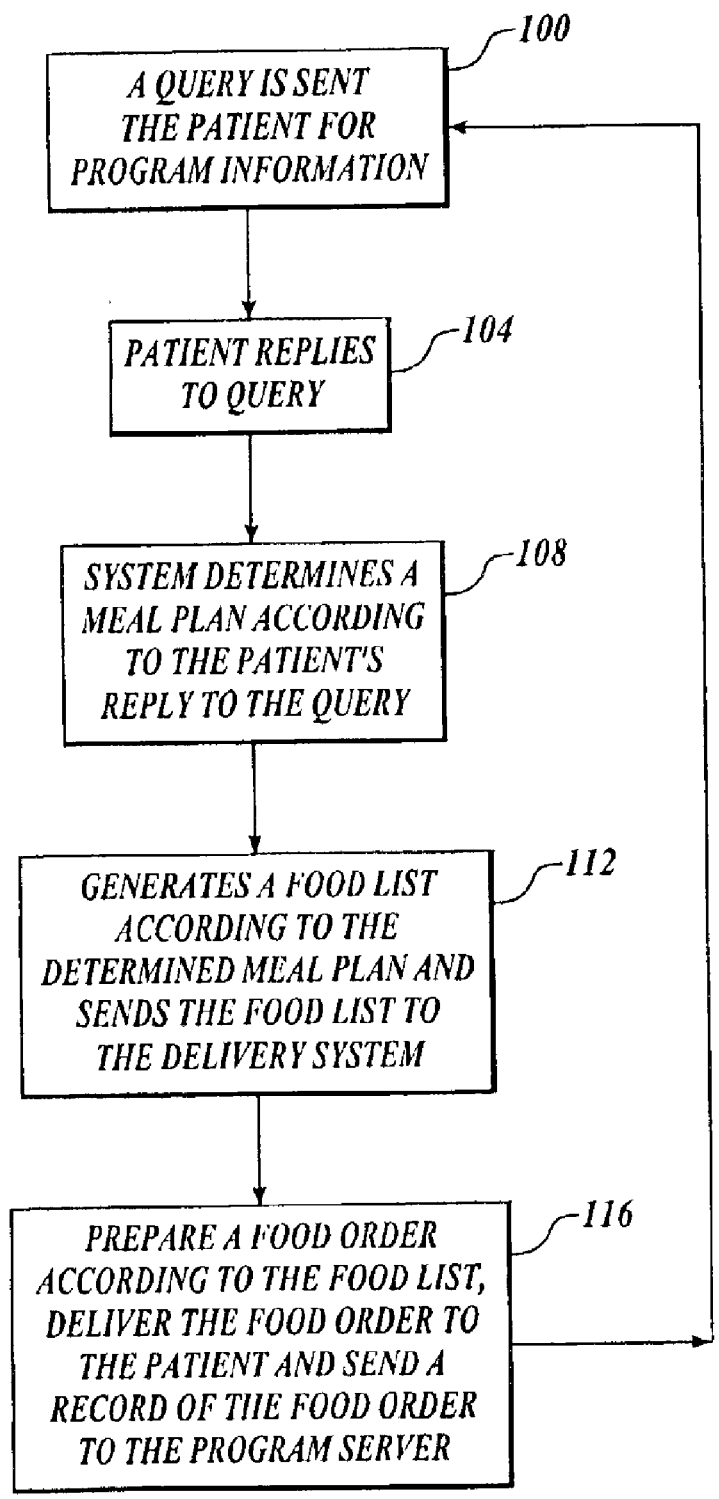
FIG. 2 is a flow diagram of the method performed by the present invention.

FIG. 2 illustrates the process performed by the components illustrated in FIG. 1. First, at block 100, the program server 22 sends a query to the patients. Then, at block 104, the patients or users replies to the query by answering the query and sending the answers to the program server 22. At block 108, the program server 22 determines a meal or diet plan for each patient according to the patient's reply to the query and previous food order information. Next, at block 112, the program server 22 generates a food list according to the determined meal or diet plan and sends the food list to the delivery system 24. Finally, at block 116, the delivery system 24 prepares a food order according to the food list, delivers the food order to the patient and sends information regarding the food order to the program server 22. After block 116, the process returns to block 100.

The program server 22 generates or prepares food lists based on specific goal achievement, such as reducing fat intake to 20%, lowering cholesterol to 100, losing 10 pounds, etc. As such, the program server 22 must calculate food intake and then determine a list of foods that fits into the meal plan based on the calculated food intake.

The queries sent by the program server 22 provides questions that allow the program server 22 to determine each patient's goals and preferences, monitor each patient's weight, diet choices, satisfaction with the food items in the food order and food choices available on the meal plan, allow patients to make food substitutions and present to the patient special offers and financial incentives to make food choices, as determined by the program server 22 from information received from the delivery system 24, prestored pricing information or some other pricing source. The queries also include, depending upon when the query occurs, a hierarchy of user interface windows, such as those in the HTTP format. These windows include links to patient information, program adherence, food choices, etc. The links when activated by the patient send the patient to other pages or window generated by the program server.

In another embodiment, the program server 22 also tracks various types of data for market research that will enable researchers to learn more about the interaction between disease and diet.

In still another embodiment, the program server 22 keeps track of the progress of a group of participants and feeds back combined progress information to an individual participant. This makes small individual changes seem more important and helps motivate the patient. For example: a diet patient receives the following message from the program server 22: "the weight club of Northern California lost 900 pounds today! Keep up the good work!" The user device 20 can alternately be a remotely programmable appliance, such as a Health Buddy made by Health Hero Network, that is updated, monitored, and reprogrammed according to protocols assigned to the patient at the program server 22. The remotely programmable appliance is remotely manipulatable by the operator administering the diet through the program server 22.

The following is an example of a diet program interaction using the process illustrated in FIG. 2. The first query from the program server includes the following questions:

How much do you weigh?

How tall are you?

How old are you?

How much do you exercise?

What is your weight goal? After the program server receives the participant's reply to the query, the program server assesses the participant's profile information determines a diet plan according to the participant's profile information. The program server sends the participant the following response that includes another query:

Your ideal weight is 170.

You can lose 10 pounds in less than 3 months if you stick to a 1500 calorie 20% fat diet.

Would you like help assembling a grocery list for this diet?

Here are the selections for breakfast ...

Here are the selections for lunch ...

Here are the selections for dinner ...

Press OK to confirm or CANCEL to delete a selection.

Would you like to review your 1500 calorie meal plan?

Shall we shop for groceries now?

We have assembled the following food basket for you:
  Steak
  Peas
  Lettuce

Press OK to order, REVIEW to edit selections

When would you like this order delivered?

Available delivery times this week are:
  Wednesday AM
  Thursday PM

What is your weight today?

Have you been sticking to your meal plan?

Would you like some new diet ideas?

We have a great prepared chef special of lean turkey casserole with a side order of beans. Shall we add the recipe and food items to your next delivery?

How do you like the Total Raisin Bran cereal?
  GOOD BAD TRY ANOTHER 9 out of 10 people on your diet have really enjoyed Healthy Start cereal.

Would you like to add it to your shopping list?
  YES NO

The program server sends the following after a reply by the patient that they want the Thursday PM delivery time.

Your next delivery is scheduled for 7:00 PM Thursday.
  REVIEW ORDER

The patient, or dieter in the example above, can also select food items from a food list presented on a web site, or the user can express some preferences based on food choices presented on the web site. The user's selections or expressed preferences are then used by the program application to generate a diet regimen. The user's food selections or preferences could also be mailed in, and entered at the program server 22 and used accordingly.

The present invention as described and shown by example above measure and reward user adherence to a healthy diet while making it convenient and easy to learn about and try new foods that are acceptable to the user's diet program and their measured intake.

While the preferred embodiment of the invention has been illustrated and described, it will be appreciated that various changes can be made therein without departing from the spirit and scope of the invention.

What is claimed is:

1. A method comprising:
  generating a query at a server system;
  sending the generated query to a user system coupled to the server system over a network; responding to the query;
  sending the responses to the query from the user system to the server system;
  determining a user's diet program information based upon the query responses, user profile information and a signal from a medical monitoring device measuring a medical condition of a user;
  generating a food delivery request at a food delivery system coupled to the server system over the network according to the determined diet program information;
  preparing a food order according to the generated food delivery request; and
  delivering the food order to the user; and sending a record of the food order to the server system.

2. The method of claim 1, further comprising storing the record of the food order at the server system.

3. The method of claim 1, further comprising suggesting one or more alternate food items for one or more of the selected food items.

4. The method of claim 1, entering point values for food items consumed by the user, sending the entered point values to the server system, comparing at the server system the received point values to predetermined meal plan limits and creating a meal plan according to the comparison.

5. The method of claim 1, further comprising scanning a bar code present on packages of user consumed food items, sending the scanned bar code information from the user system to the server system, automatically ordering refills according to program information, recording the scanned food item as being consumed, and updating the program information according to the recorded scanned food item.

6. The method of claim 1, further comprising generating a program adherence value based on the program information, any predefined program goals and the responses to the query.

7. A system comprising:
  a user system comprising a processor, memory and at least one medical monitoring device, the medical monitor device configured to send a signal measuring a medical condition of a user to the processor;
  a server system comprising a processor and memory, the server system being coupled to the user system over a network; and
  a food delivery system coupled to the server system over the network,
  wherein the server system generates and sends a query to the user system, the server system determines diet program information for the user associated with the user system based upon responses to the query sent from the user system to the server system, the user profile information, the signal measuring the medical condition of the user, and generates a food delivery request according to the determined diet program information, and
  wherein the food delivery system prepares a food order according to a food list, delivers the food order to the user, and sends a record of the food order to the server system.

8. The system of claim 7, wherein the medical monitoring device includes a weight scale, a blood glucose meter, and a peak flow meter.

9. The system of claim 7, wherein the signal measuring a medical condition include obesity, diabetes, and asthma medical conditions.

10. The system of claim 7, wherein the query to the user system includes obesity, diabetes, and asthma related queries.

11. The system of claim 7, wherein the food list includes foods appropriate to treat the medical condition.

12. The system of claim 11, wherein the medical condition includes obesity, diabetes, and asthma.

13. A computer readable medium for performing a method comprising:

generating a query at a server system;

sending the generated query to a user system coupled to the server system over a network; responding to the query;

sending the responses to the query from the user system to the server system;

determining a user's diet program information based upon the query responses, user profile information and a signal from a medical monitoring device measuring a medical condition of a user;

generating a food delivery request at a food delivery system coupled to the server system over the network according to the determined diet program information;

preparing a food order according to the generated food delivery request; and delivering the food order to the user; and sending a record of the food order to the server system.

* * * * *